United States Patent
Seaton, Jr. et al.

(10) Patent No.: US 8,524,798 B2
(45) Date of Patent: Sep. 3, 2013

(54) MATERIALS AND APPARATUS FOR IN-SITU BONE REPAIR

(76) Inventors: James P. Seaton, Jr., Chatham, NJ (US); Ralph W. Carmichael, legal representative, Phoenix, AZ (US); Linda M. Trebing, Wayne, PA (US)

( * ) Notice: Subject to any disclaimer, the term of this patent is extended or adjusted under 35 U.S.C. 154(b) by 102 days.

(21) Appl. No.: 11/861,246

(22) Filed: Sep. 25, 2007

(65) Prior Publication Data

US 2008/0086143 A1 Apr. 10, 2008

Related U.S. Application Data

(63) Continuation-in-part of application No. 11/078,146, filed on Mar. 11, 2005, now abandoned, and a continuation-in-part of application No. 11/729,231, filed on Mar. 28, 2007, now abandoned.

(60) Provisional application No. 60/847,214, filed on Sep. 25, 2006, provisional application No. 60/860,540, filed on Nov. 21, 2006, provisional application No. 60/553,100, filed on Mar. 15, 2004, provisional application No. 60/791,542, filed on Apr. 12, 2006.

(51) Int. Cl.
*A61K 6/083* (2006.01)
*A61K 6/08* (2006.01)
*A61K 6/00* (2006.01)
*A61K 6/02* (2006.01)
*C08F 2/50* (2006.01)
*C08J 3/28* (2006.01)

(52) U.S. Cl.
USPC ........... 523/121; 523/105; 523/112; 523/113; 525/264; 525/266; 525/267; 525/268; 252/182.11; 252/182.12; 252/182.13; 252/182.14; 252/182.17; 623/16.11; 623/23.48; 623/23.51; 623/23.5; 623/23.61; 623/23.6; 623/23.62

(58) Field of Classification Search
USPC .............. 623/16.11, 23.48, 23.51, 23.5, 23.6, 623/23.61, 23.62; 525/2, 261, 264, 266, 525/267, 268, 588, 650, 730, 731; 523/1, 523/105, 17, 113, 115
See application file for complete search history.

(56) References Cited

U.S. PATENT DOCUMENTS

| | | | | |
|---|---|---|---|---|
| 3,829,903 | A * | 8/1974 | Stati et al. | 600/36 |
| 4,245,623 | A * | 1/1981 | Erb | 128/831 |
| 5,391,590 | A * | 2/1995 | Gerace et al. | 523/107 |
| 5,718,586 | A * | 2/1998 | Sharp et al. | 433/214 |
| 6,136,039 | A * | 10/2000 | Kristinsson et al. | 623/36 |
| 2002/0169505 | A1* | 11/2002 | Jethmalani et al. | 623/6.56 |
| 2005/0075533 | A1* | 4/2005 | deVries | 600/29 |
| 2005/0209695 | A1* | 9/2005 | de Vries et al. | 623/17.11 |
| 2006/0111792 | A1* | 5/2006 | Shannon | 623/36 |
| 2007/0179620 | A1* | 8/2007 | Seaton et al. | 623/17.16 |

* cited by examiner

*Primary Examiner* — Sanza McClendon (57) ABSTRACT

Compositions for use in treating and repairing orthopedic defects are provided. The compositions are especially useful for performing percutaneous vertebroplasty, percutaneous kyphoplasty and other procedures. When cured, the compositions are relatively solid but compressible, and prior to curing are viscous liquids with a low enough viscosity to fill voids in cavities such as voids within fractured vertebrae. Optionally, the properties of a composition according to the invention can be adjusted taking into account the hardness and density of the orthopedic structure to be repaired. Also disclosed are devices and methods for using the compositions, and a kit containing components for forming and utilizing the composition.

12 Claims, 7 Drawing Sheets

# MATERIALS AND APPARATUS FOR IN-SITU BONE REPAIR

CROSS-REFERENCE TO RELATED APPLICATIONS

This application claims priority to U.S. Provisional Patent Application Ser. No. 60/847,214, filed Sep. 25, 2006, U.S. Provisional Patent Application Ser. No. 60/860,540, filed Nov. 21, 2006, and is a continuation-in-part of U.S. Utility application Ser. No. 11/078,146 filed Mar. 11, 2005 now abandoned, (which claims priority to U.S. Provisional Patent Application Ser. No. 60/553,100 filed Mar. 15, 2004), and is also a continuation-in-part of U.S. Utility application Ser. No. 11/729,231 filed Mar. 28, 2007 now abandoned, (which claims priority to U.S. Provisional Patent Application Ser. No. 60/791,542 filed Apr. 12, 2006). The respective disclosures of the forgoing applications that are not inconsistent with this application are incorporated herein by reference.

TECHNICAL FIELD

The present invention relates to compositions for treating and repairing skeletal defects and injuries, such as vertebral fractures, and osteolysis of the spine due to osteoporosis (collectively referred to as "skeletal defects"). This invention also relates to devices and methods for using the compositions to treat skeletal defects, particularly through the use of vertebreoplasty or kyphoplasty.

BACKGROUND OF THE INVENTION

In persons with osteoporosis, vertebral fractures occur in approximately 750,000 reported cases each year in the United States alone. These fractures can cause acute or chronic pain, reduce the quality of life, and shorten life expectancy (N. B. Watts, *Osteoporotic Vertebral Fractures*, Neurosurg. Focus. 2001 Apr. 15; 10(4): E12). Percutaneous vertebroplasty ("PVP") and percutaneous kyphoplasty ("PKP") are minimally invasive options used to treat vertebral fractures and osteolysis.

PVP involves stabilizing a fracture by injecting a bone cement into the inter-trabecular marrow space of a fractured vertebra, usually under fluoroscopic or other radiological guidance. In PKP a balloon is inserted into the inter-trabecular marrow space of the damaged vertebra, which is then inflated to restore the fractured vertebra as much as possible to its original shape. The balloon is then deflated and removed, and the cavity formed is filled with bone cement. In both methods the injected bone cement functions as a supportive material that to some extent fills voids and stabilizes the vertebral body.

The most commonly used bone cements include polymethyl methacrylate (PMMA). These cements are prepared by mixing methyl methacrylate powder and a radiopaque agent with liquid monomer. Once mixed, the bone cement is injected under radiological imaging into the vertebral body where it cures in situ into a hardened material. Although widely used, PMMA bone cements have a number of disadvantages including one or more of the following:

(1) They are hard and stiff and are suspected of contributing to adjacent level fractures in other vertebrae following PVP or PKP.

(2) Because of their hardness, they may exert pressure on nerves and tissue causing pain and/or nerve or tissue damage.

(3) Once mixed the bone cement is often very thick, difficult to inject into the body and does not completely fill the spaces into which it is injected.

(4) The mixing of the cement components is done by a doctor or other person (hereafter, "user") at the location (such as a hospital) where PVP or PKP is performed. The mixing is susceptible to error, particularly (a) the addition of excess monomer, which is toxic and may cause adverse reactions (such as pulmonary embolism or hypotensive reaction that can cause respiratory or cardiac failure, which can lead to death), or (b) the addition of too little monomer, which will cause the cement to be thick, to harden too quickly, and make it difficult to inject into the body.

(5) The mixing of the PMMA cement components can be uncomfortable for the user due to strong, unpleasant odors generated during the process. Some users have had to incur the expense and burden of installing exhausting vent hoods within their operating rooms to deal with this problem.

(6) The in situ curing of the cement is exothermic, which can lead to necrosis of the surrounding tissue thereby harming a subject being treated.

(7) PMMA bone cements usually are porous and can absorb water, which leads to degradation of the bone cement over time.

(8) Once injected into the vertebral body, PMMA bone cements tend to form lumps of material within the vertebral body rather than evenly filling the space in the vertebral body.

(9) PMMA bone cement does not adhere well to bone.

(10) PMMA bone cement tends to physically displace the trabeculae during injection and curing.

(11) PMMA bone cement does not allow the user to easily stop and start the injection procedure once it has begun.

Thus, PVP and PKP would benefit from an injectable composition of biomaterial that does not have the problems associated with the use of PMMA bone cements or bone cements with problems similar to those of PMMA bone cements. Another optional benefit would be obtained if the device used to mix and/or inject the composition of biomaterial eliminated the requirement of the user having to mix the components that form the composition.

SUMMARY OF THE INVENTION

The present invention relates to compositions for use in procedures, such as PVP or PKP, in the body of a living being, particularly a human (hereafter, "patient"), and to methods and devices related to using the compositions. The compositions, methods and devices may also be used to fill bone or tissue defects in other parts of the body.

One aspect of the present invention relates to an injectable composition that cures in situ to treat skeletal defects, particularly through PVP or PKP. The composition is preferably a silicone elastomer formed from a mixture of two viscous liquid components: (1) one or more polysiloxanes containing one or more catalysts ("component A"); and (2) one or more polysiloxanes containing one or more cross-linking agents ("component B"). The polysiloxanes may be reinforced with an additive such as amorphous silica. In preferred compositions these two components are mixed in equal parts (i.e., a 1:1 weight ratio), but can be mixed in any suitable ratio that yields a composition with properties as described herein. Components A and B are mixed just prior to injection into the body to form a flowable, viscous composition, which is then injected into the body where it cures in situ to a generally solid, rubbery consistency.

Compositions according to the invention preferably include a platinum (Pt) catalyst and polymerize in situ in about 3-15 (preferably about 3-8 and most preferably about 3) minutes at body temperature and are essentially not resorbable (which means they are essentially not absorbed into the body). Thus, they remain in place to fill the void they occupy.

Compositions of the present invention have compressive characteristics that are closer to those of vertebrae than bone cement utilizing PMMA, which is harder and stiffer than vertebrae. Further, the durometer of compositions of the invention can be adjusted for a particular application taking into account the bone quality and/or density of the affected area. Typical compositions of the present invention have a Shore A durometer value in the range of 15 to 90, or in the range of 20 to 70, or in the range of 20 to 60.

Compositions according to the invention may optionally comprise a compound to provide radiopacity. If used, the radiopaque component is preferably added to both components A and B, but may be added to just one component. In preferred embodiments, the compositions of the invention comprise barium sulfate ($BaSO_4$) or other suitable radiopaque compound added preferably at about 15% by weight, but can vary within a preferred range of about 10% to 40% by weight.

The invention also includes a device and device kit for mixing and dispensing the composition for use in medical procedures. The system comprises a pre-filled, two-part mixing and dispensing cartridge. The mixing and dispensing cartridge keeps component A and component B separate until time of use, at which time each of the components is delivered via pressure into and through a mixing tip, which is preferably static and includes helical elements to mix the components together as they are pushed through the tip. The mixed components form a composition according to the invention that is a viscous liquid (since the composition has not yet cured), which is pushed via the pressure out of the tip, through a tube or line and injected into the body. The system provides the ability for the user to stop a procedure and resume it with minimal effort by simply disconnecting the existing tubing and mixing tip, releasing the system pressure (which is preferably applied by the user's hand squeezing a trigger as explained in more detail below) purging the system and reattaching a new mixing tip and tube.

A method according to the invention forms a composition that has a relatively uniform ratio of components and relatively uniform material properties. Since the ratio of component A and component B is essentially fixed by the operation of the device, the risk of the end user detrimentally altering the ratio is virtually eliminated.

A composition according to the present invention provides at least one or more of the following benefits: (1) low toxicity; (2) it is injectable and has a viscosity that allows it to flow into voids or spaces; (3) it is biocompatible and non-toxic; (4) it is generally non-porous so is unlikely to absorb much water; (5) it may be utilized in conjunction with a device as described above that provides consistent component mixing to produce a generally uniform composition; (6) it cures in situ with little or no exothermic reaction; (7) it may be formulated and mixed to have a specific durometer taking into account factors such as the relevant bone hardness and density; (8) it provides better interdigitation than prior art materials; (9) it does not show significant shrinkage when cured; and (10) it does not contain methyl methacrylate monomer so does not demonstrate the problems associated with releasing toxic fumes or of uncured toxic monomer remaining in the body.

DETAILED DESCRIPTION OF PREFERRED EMBODIMENTS

One aspect of the present invention relates to injectable compositions that cure in situ and are used in treating and repairing skeletal defects, such as through PVP and/or PKP procedures, to repair damaged vertebrae. Other applications for a composition according to the invention include the filling of bone-voids and repair of intervertebral discs.

One preferred composition according to the invention comprises two flowable components including: (1) one or more polysiloxanes and one or more catalysts (previously defined as "component A"); and (2) one or more polysiloxanes and one or more cross-linking agents (previously defined as "component B"). The polysiloxanes may be reinforced with an additive such as amorphous silica. The catalyst is most preferably platinum and the cross-linking agent is preferably trimethyl methyl-hydrodimethyl siloxane, although any suitable catalyst(s) or cross-linking agent(s) may be used. The preferred embodiment utilizes a platinum catalyst, which yields benefits over other catalysts, such as tin. The platinum catalyst (1) enables the composition to have a longer shelf life, (2) is less toxic in the body than some other catalysts (such as tin), and (3) results in the final composition being less brittle.

In preferred compositions, component A and component B are mixed in equal parts (i.e., a 1:1 weight ratio), although any suitable ratio may be used) to form a flowable, viscous composition that is then injected into the body where it cures into a silicone elastomer.

The compositions of the present invention are fully cured in situ (after injection into a damaged vertebra, other bone or body structure) in about 3 to 15 minutes, and more preferably in about 3 to 8 minutes, most preferably in about 3 minutes, at body temperature. The viscosity of a composition immediately after components A and B are mixed is preferably about 100,000 cps, but can vary within a preferred range of about 100,000 cps to 180,000 cps, although the composition may have any suitable viscosity that enables the composition to be injected into the body and sufficiently fill voids.

The compositions of the present invention optionally comprise a compound to provide radiopacity. The radiopaque additive may be added to either or both components, either prior to or as they are mixed to form the composition that is injected into a vertebral body or other skeletal body. Preferably, the radiopaque additive comprises between about 10% and 40% by weight, and most preferably about 15% by weight (also referred to as "w/w"), of the entire composition after mixing, although any suitable amount may be used and can vary depending upon the type of additive and the application for which the composition will be used. Suitable radiopaque materials include those selected from one or more of the group consisting of silver powder, barium sulfate, bismuth trioxide, zirconium dioxide, tantalum or titanium powders or fibers, calcium sulfate, calcium phosphate, hydroxyapatite, tri-calcium phosphate, and other medically appropriate opacifier additives. In preferred embodiments, barium sulfate is added at about 15% by weight to both components A and B to provide the desired radiopacity. The addition of a radiopaque material to the compositions allows the injection of the mixed composition into the disc to be monitored with standard fluoroscopic visualization techniques. One advantage of materials of the present invention is that because the compositions are naturally radiopaque the percentage of radiopaque additive needed to provide the desired degree of radiopacity is less (often about half) than that required in PMMA based bone fillers.

The catalyst for initiating cross linking and curing is preferably platinum metal in a weight percent of the total composition of between 0.0005% and 0.010%, and most preferably greater than 0.001%, although any suitable weight percentage will suffice as long as the resulting composition yields one or more of the benefits set forth herein. The concentration of catalyst may also be expressed in units of parts per million (ppm). For example, in one embodiment, the concentration of the platinum catalyst is preferably 15 ppm in component A prior to mixing and subsequently 7.5 ppm in the mixed composition. In alternate embodiments, other catalysts may be used, such as tin.

A preferred composition for the composition according to the invention (Example 1) is formed by mixing together the following component A and component B.

Component A:
from 50% to 75% vinyldimethyl terminated dimethylpolysiloxane/trimethylsiloxy terminated polydimethyl siloxane (in preferably a 1:1 ratio by weight),
from 10% to 30% amorphous silica,
10% to 40% radiopaque additive, and
greater than 0.001% Pt catalyst.
[Note: all percentages are weight %.]
Component B:
from 50% to 75% vinyldimethyl terminated dimethylpolysiloxane/trimethylsiloxy terminated polydimethyl siloxane (in preferably a 1:1 ratio by weight),
from 10% to 30% amorphous silica,
10% to 40% radiopaque additive, and
from 0.5% to 5% trimethyl methyl-hydro dimethyl siloxane (cross linking agent).
[Note: all percentages are weight %.]

Component A and component B may be intermixed in ratios depending on the desired consistency of the cured composition, for instance, component A and component B may be intermixed in the ratios of 0.1:1 to 1:0.1 by weight.

Another preferred embodiment of a composition (Example 2) is formulated with the following ranges of components:
Component A:
64% vinyldimethyl terminated dimethylpolysiloxane/trimethylsiloxy terminated polydimethyl siloxane (in preferably a 1:1 ratio by weight),
21% amorphous silica,
15% barium sulfate powder, and
greater than 0.001% Pt catalyst.
[Note: all percentages are weight %.]

Component B:
63% vinyldimethy terminated dimethylpolysiloxane/trimethylsiloxy terminated polydimethyl siloxane (in preferably a 1:1 ratio by weight),
21% amorphous silica,
15% barium sulfate powder
1% trimethyl methyl-hydro dimethyl siloxane (cross linking agent).
[Note: all percentages are weight %.]

Component A and component B may be intermixed in ratios depending on the desired consistency of the cured composition, for instance, component A and component B may be intermixed in the ratio of about 1:1 by weight.

Each of the above preferred compositions is a silicone elastomer composition, and after curing has about 60-85% by weight poly dimethyl siloxane, about 0.5%-5% cross linking agent, about 10 to 20% dilutent, and about 10 to 20% radiopaque material, all based on the weight of the entire composition. Compositions preferably have a working time (i.e., from the mixing of component A and component B to the time the composition completely cures) of between 2-20 minutes, and preferably between 3-15 minutes, more preferably between 3 and 8 minutes and most preferably about 3 minutes.

The hardness (durometer) of a composition of the present invention can be altered depending upon the application for which it will be used. Factors such as the density and hardness of the bone of the affected area where the composition is to be applied may be taken into consideration when determining the durometer. Typical compositions of the present invention have a Shore A durometer value in the range of 15 to 90, or in the range of 20 to 70, or in the range of 20 to 60. A composition having a durometer value below 15 Shore A does not have the desired properties for repair of vertebrae or bones, but may be used for intervertebral discs. Disc augmentation may be performed using the composition and system of the present invention when the composition is of an appropriate durometer in the range of 15 to 90.

STUDIES

Embodiments of compositions of the present invention have been characterized by the following tests.

Biocompatability Studies

Table 1 summarizes biocompatibility evaluation data for compositions of the present invention formed using component A and component B as described above. Testing was carried out using standard procedures known to those skilled in the relevant art.

TABLE 1

Summary of Biocompatibility Evaluations Completed

| Study Title | Test Material | Results |
| --- | --- | --- |
| Cytotoxicity - MEM elution | Silicone | Non-cytotoxic. |
| Guinea Pig Maximization Test | Silicone | Test article did not show evidence of causing delayed dermal contact sensitization in a guinea pig model. |
| USP Intracutaneous Toxicity Study in Rabbits | Silicone | No evidence of significant irritation or toxicity from the extracts. |

TABLE 1-continued

Summary of Biocompatibility Evaluations Completed

| Study Title | Test Material | Results |
|---|---|---|
| USP Systemic Toxicity Study in Mice | Silicone | No mortality or evidence of systemic toxicity from the extracts. |
| USP Muscle Implantation Study (with histopathology) in the Rabbit (90 days) | Silicone | Macroscopic reaction was not significant compared to control; Microscopic analysis classified as a slight irritant as compared to control. |
| Ames Mutagenicity Study of a Saline Extract | Silicone | Non-mutagenic. |
| Ames Mutagenicity Study of a DMSO Extract | Silicone | Non-mutagenic. |
| In vitro hemolysis study | Silicone | Non-hemolytic. |
| Chronic Toxicity and Carcinogenicity Study in Rats with Misty Textured Shells (A) and (D), Responsive Silicone Gel (B) and Silicone Elastomer Dispersion, RTV (C) Subcutaneous Implants | Silicone (group A&D) | No evidence of systemic toxicity. |
| Cytotoxicity, Hemolysis, Pyrogenicity - MEM elution | Silicone + Barium | Non-cytotoxic. Non-hemolytic. Non-pyrogenetic. |

Gel (Dough) Time and Setting Time

The gel time for a preferred composition according to Example 2, above, was measured over a time period of 1-5 minutes at a range of room temperatures between 15.6° C./60° F. and 35° C./95° F. As a point of comparison, gel time for a silicone elastomer corresponds to the dough time for a PMMA polymer. The setting time for the composition was measured over a time period of 5-15 minutes at temperatures between 60° F. and 85° F., and at approximately 3 minutes at 95° F. (in order to provide a conservative estimate of setting time at body temperature). The results are summarized in the following table:

| Temp ° F. | Gel Time | Set Time |
|---|---|---|
| 95 | 0:55 | 2:45 |
| 95 | 1:00 | 3:20 |
| 83 | 1:20 | 5:12 |
| 83 | 1:35 | 5:20 |
| 74.7 | 1:45 | 6:10 |
| 74.6 | 1:55 | 5:40 |
| 60 | 4:50 | 14:40 |

Viscosity, Pre-Gel (Pre-Dough) Stage Extrusion

In this test according to section 7.8.5 of ASTM F451-99, a composition formed of component A and component B was injected into a cylindrical mold with four 1 mm-diameter holes in the bottom, and allowed to cure under a 1 lb. load. The composition viscosity was about 168,000 cps when injected. After curing, the material was removed from the mold and the sample was evaluated to see how well the material flowed into the holes at the bottom of the mold. This testing demonstrated that the composition completely filled in the holes, indicating excellent intrusion properties (and thus ability to fill voids in vertebrae or other body structures).

Molecular Weight

The weight average molecular weight of the base polymer in component A and component B, vinyldimethyl terminated dimethyl polysiloxane/trimethylsiloxy terminated polydimethyl siloxane (in a 1:1 ratio in this preferred embodiment), was determined to be about 71,000 and the number average molecular weight about 29,000. The weight average molecular weight of the cross linking agent in component B, trimethyl methyl-hydro dimethyl siloxane, was determined to be about 10,569 and the number average molecular weight about 5,043.

Maximum Polymerization Temperature

The temperature of two samples of the preferred composition formed from component A and component B at room temperature (23.9° C./75° F.) were monitored throughout the curing process. The maximum temperature reached was 26.2° C./79.2, and the maximum total temperature increase was 2.0° C./3.6° F. The results are summarized in the table below.

| | Test #1 | Test #2 |
|---|---|---|
| Minimum Temp. (° C./° F.) | 24.7/76.5 | 24.2/75.6 |
| Maximum Temp. (° C./° F.) | 25.9/78.6 | 26.2/79.2 |
| Gel (Dough) Time (sec) | 105 | 115 |
| Setting Time (sec) | 370 | 340 |
| Total Temp. increase (° C./° F.) | 1.2/2.2 | 2.0/3.6 |

Mechanical Testing

One beneficial performance characteristic for a composition used in PVP or PKP is the ability to sustain compressive loading. In mechanical testing and/or cadaver testing an embodiment of the composition described herein demonstrated compressive load carrying properties that are equivalent to bone. The force needed in axial loading to cause deflection was also similar to bone. Testing also showed no significant deterioration of the mechanical properties of the composition under accelerated aging conditions.

Dispensing and Mixing Device

Another aspect of the invention relates to devices for mixing and dispensing a composition according to the invention for use in medical procedures. Once the mixing process has been completed in the helical element the composition continues to flow through a nozzle (or mixing element) and line where it is immediately injected into the affected vertebral body or other area being treated using standard percutaneous techniques known to those skilled in the art.

Figure 1:
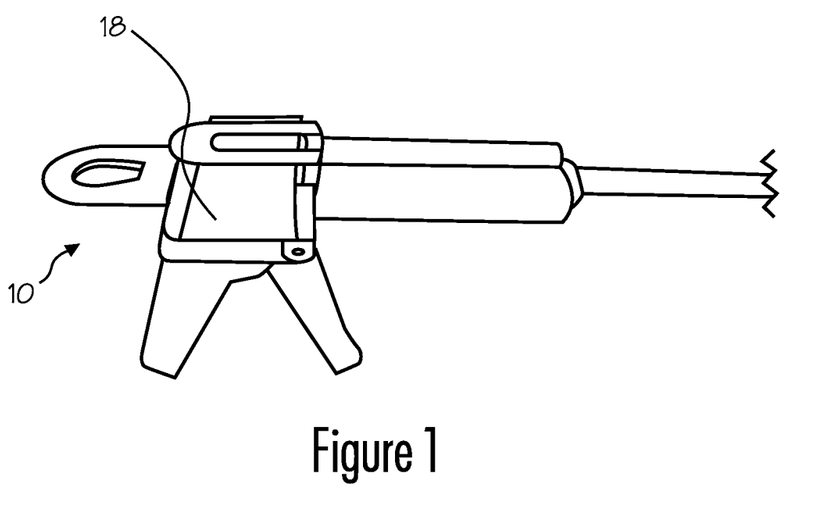
FIG. 1 shows one embodiment of a mixing and dispensing device according to an embodiment of the invention.

A mixing and dispensing device (10) according to one embodiment of the present invention is shown in FIG. 1. The pre-filled dispensing system (10) comprises a pre-filled cartridge (12) containing, in the illustrated embodiment, two side-by-side, pre-filled chambers (14) and (16), one of which (14) contains component A comprising a catalyst and the other of which (16) contains component B comprising a cross-linking agent. The total volume of material in each pre-filled cartridge is preferably between about 20 and 70 ml, and more preferably between about 35 to 40 ml. The respective mixing and dispensing cartridges keeps component A and component B separate until time of use, at which time the contents of the chamber containing component A and the contents of the chamber containing component B are delivered into the mixing element (20).

In the illustrated embodiment, the two respective chambers are of equal volume and a plunger (not shown) is used to apply equal pressure to each chamber through application of a squeezing force preferably applied by the user's hand to the dispenser trigger/handle assembly (18) at the bottom of dispensing system (10). In this embodiment, as pressure is applied equal amounts of component A and component B are pushed into and through the mixing element (20) and mixed together to form a liquid composition for injection into a treatment space such as a volume defined within a bony structure (such as the interior of a vertebra) in the body.

Figure 2:
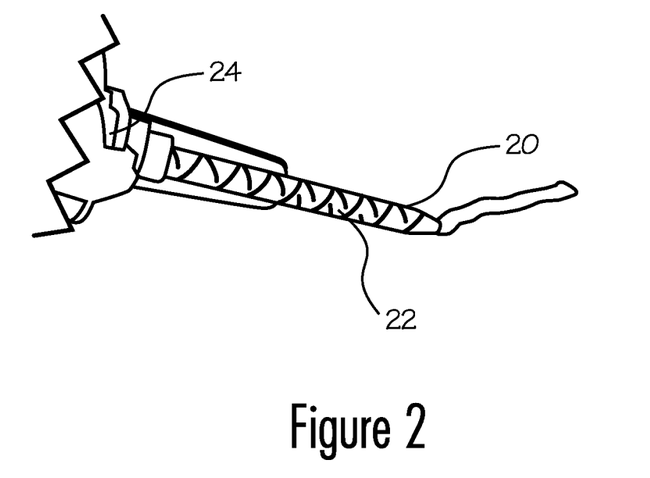
FIG. 2 shows the static mixing element of the device shown in FIG. 1 demonstrating the mixing and blending action.

FIG. 2 shows a close-up of a static mixing element (20) of a dispensing system according to the invention. Although this preferred embodiment shows a static, helical mixing element (20), any suitable mixing element may be used. The static mixing element (20) has a helical geometry (22) disposed in a cavity inside the element that mixes component A (including the catalyst) and component B (including the cross linking agent) in the desired ratio to form a composition, which is then immediately injected at the time of PVP, PKP or other procedure into the body using the same pressure that pushed component A and component B out of their respective chambers and through the mixing element (20).

The connecting end of the static mixing element (20) is attached to the output end of pre-filled cartridge (12) by rotatably engaging a locking bayonet fitting (24). The dispensing system (10) and mixing element (20) ensure that components A and B are mixed to the proper injection consistency before being dispensed from the dispensing system (10) and into the body.

Thus, by using a pre-filled cartridge that communicates with a mixing element, and by pushing predetermined amounts of component A and component B through the mixing element, a relatively uniform and constant composition is achieved.

Figure 3:
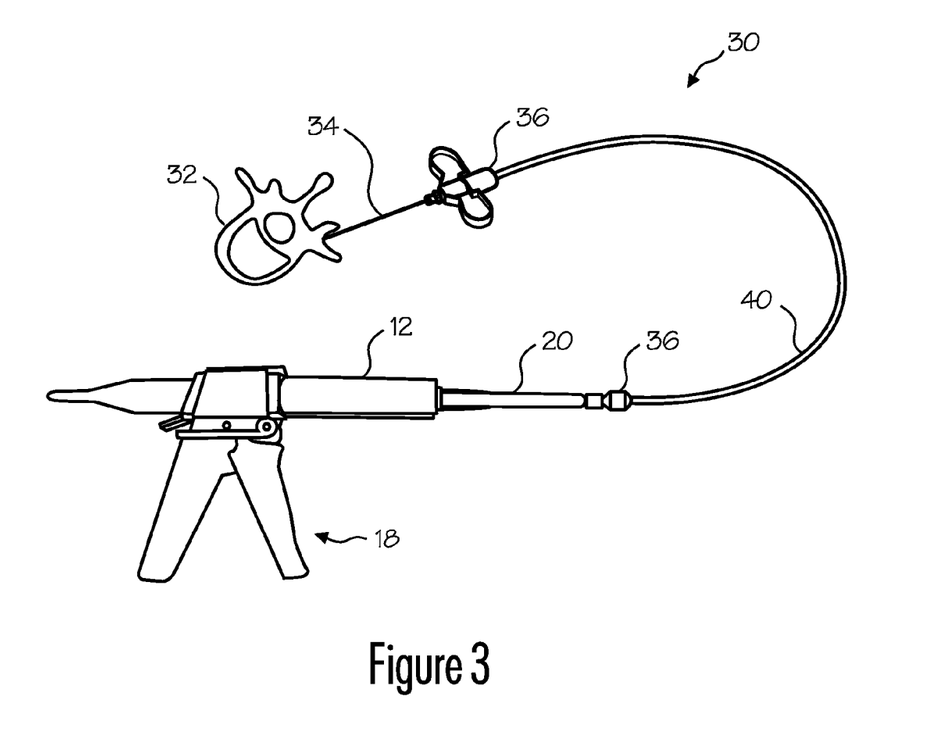
FIG. 3 shows an embodiment of the dispensing device of FIG. 1 configured for injecting into a vertebra.

FIG. 3 shows a device application configuration (30) according to one embodiment of the present invention. As described above in relation to FIG. 1, squeezing pressure applied to the dispenser trigger/handle assembly (18) advances material from the pre-filled cartridge (12) in a desired ratio (such as 1:1), into the static mixing element (20). Attached to the end of the static mix element (20) by luer-lock adapters (36) is extension tubing (40). The other end of the extension tubing is attached via a luer-lock adapter (36) to an appropriately sized trocar (34) that is inserted into a vertebral body such as the model vertebra (32). After combining the two components in the desired ratio through the static mix element (20), the composition is immediately dispensed into the extension tubing (40) and injected into the vertebral body (32) via trocar (34) to fill voids and repair defects. Once injected the composition polymerizes (i.e., fully cures) in situ. The positioning of the trocar (34) in the vertebral body and filing of vertebral body with material can be monitored using fluoroscopic or other radiological guidance techniques.

The luer-lock adapters (36) are preferable high-flow, wide inner-diameter, low pressure fittings that provide improved flow of the material with reduced back pressure on the system to lessen the squeezing pressure exerted by the user on the dispenser trigger/handle assembly (18).

A mixing and dispensing device of the invention is preferably formed of any suitable materials that can be sterilized and/or sanitized. For example, the cartridge, pistons, plunger, and static mix element can be formed of a polymer such as polypropylene, while the O-ring of the pistons may be formed of viton. The dispenser can be made of a material such as glass-filled nylon.

Figure 4:
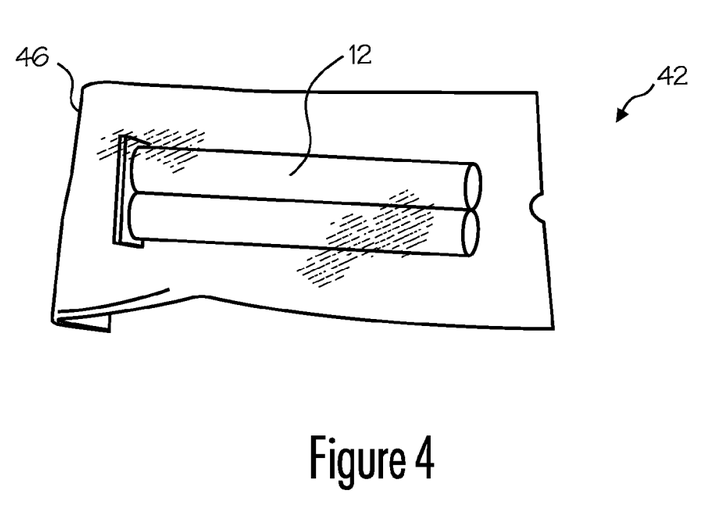
FIG. 4 shows a pre-filled cartridge (44) in sterile packaging (46) according to an embodiment of the invention.
Figure 5:
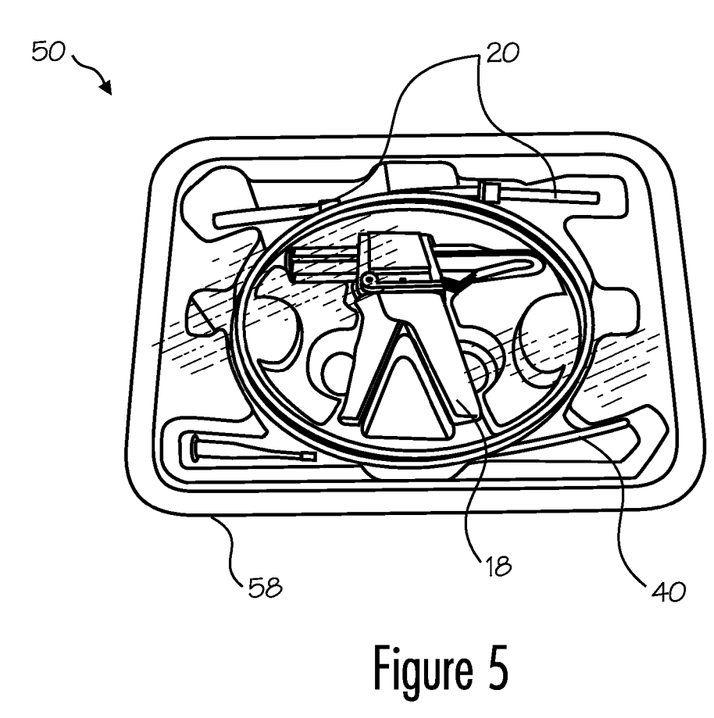
FIG. 5 shows an embodiment of packaging for the delivery device of FIG. 1 according to one embodiment of the invention, comprising a dispenser (52), static mix elements (54), extension tubing (56) and packaging (58).

FIG. 4 shows a pre-filled cartridge (12) in sterile packing (46). The preferred packaging for the pre-filled cartridge (12) is a double peel pouch of clear Mylar® (Mylar is a registered trademark of DuPont for its polyester film material) with a Tyvek® (Tyvek is a registered trademark of DuPont for its spunbonded polyolefin material) breather. Other suitable materials from other manufacturers may also be used. FIG. 5 shows a delivery system packaging (50) comprising a double blister package of clear PETG (Polyethylene Terepthalate Glycol) with Tyvek lid (58) and containing dispenser trigger/handle assembly (18) for the dispenser, static mix elements (20) and extension tubing (40).

Figure 6:
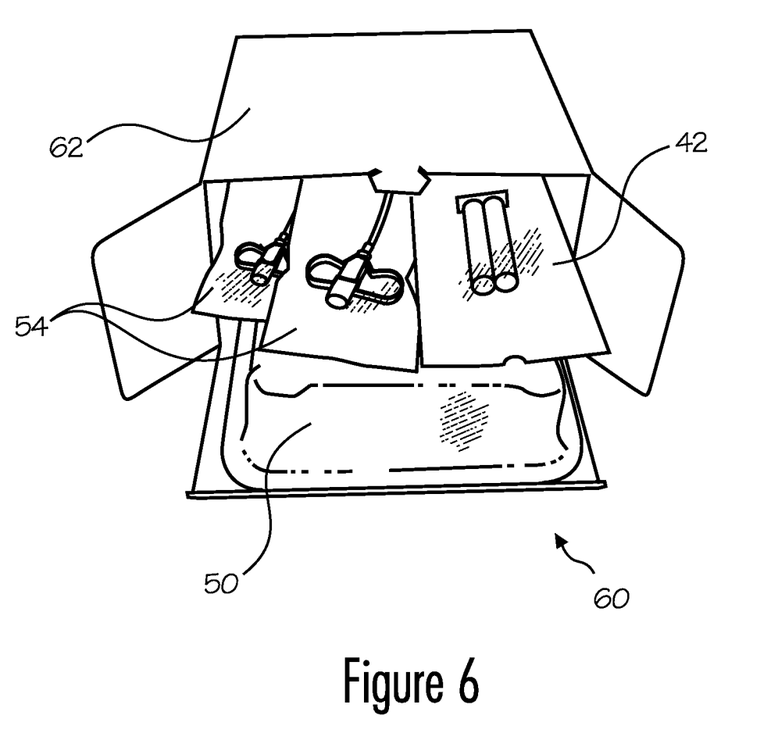
FIG. 6 shows a kit including the components of FIG. 2, wherein the kit comprises a pre-filled cartridge (42), dispensing system (50) and trocars (54).

The pre-filled cartridge dispensing systems of the present invention are preferably provided as single use kits. FIG. 6 shows a device kit (60) according to one aspect of the present invention. The sterile device kit (60) comprises three components in (preferably) sterile packaging: (1) a pre-filled cartridge (12) containing a partitioned component A chamber and a component B chamber; (2) delivery system package (50) comprised of a dispenser trigger/handle assembly (18), one or more static mix elements (20), one or more extension tube assemblies (40), and preferably, eight extension tube assemblies (40); and (3) one or more trocars (54). The components of the kit are packaged in materials that are capable of withstanding the stress associated with distribution, shipping and sterilization, and are capable of maintaining a sterile barrier for a shelf life of at least two years.

In one embodiment, each pre-filled cartridge of the dispensing system contains two chambers, which may be cylindrical in shape and are preferably located side by side. One cylinder is filled with component A and the other with component B. After the cartridge is filled and sealed, each pre-filled cartridge and its contents (component A and component B, respectively) are sterilized via a dry heat process at 121° C. for 12 hours. The degree of sterilization is performed preferably to obtain at least a $10^{-6}$ sterility assurance level ("SAL"). The sterilized cartridges are then packaged as shown in FIG. 4 and assembled into dispensing device kit (60) according to the invention.

In the illustrated embodiments, each cartridge body and the outside surface of the inner cylinders may be sterilized via ethylene oxide while the contents of the cylinders may be sterilized via a dry heat process. The sterilized, sealed cartridge is then placed into a kit (60) with the dispensing handle/trigger assembly (18) and mix nozzle (20) and other components. The external surfaces of the delivery system packaging, cartridge, dispenser handle, static mix elements, trocars, and other components of the device kit may be sterilized with an ethylene oxide sterilization process (ETO) and then the kit is assembled in the packaging described above. The closed system of the kits provides for virtually eliminating the risk of changing the composition prior to injection.

Figure 7:
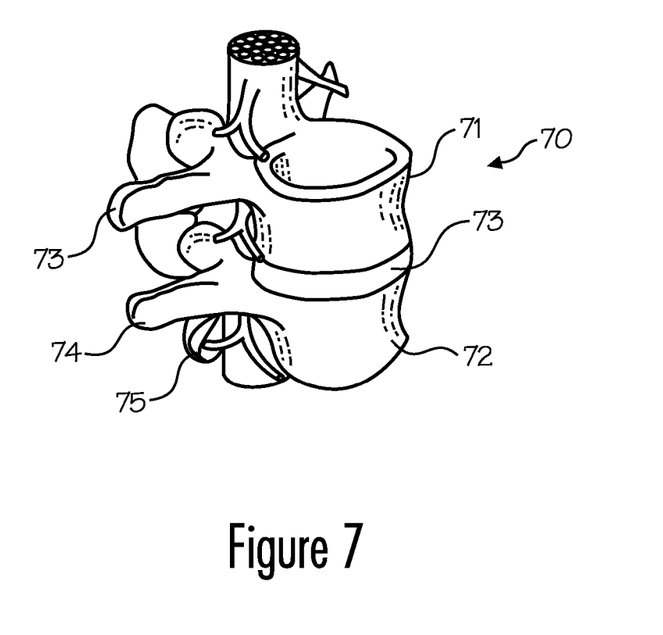
FIG. 7 shows a front perspective view of a portion of a human spinal column.

FIG. 7 shows the front perspective view of a portion (70) of a human spinal column. The spinal column portion (70) comprises a series of vertebrae (71) and (72) between which is disposed an intervertebral disc (73). Intervertebral discs generally function to maintain the proper spacing and alignment between vertebrae while also absorbing and distributing loads imposed upon the spinal column. Bone structures (73) and (74) protrude from the vertebrae forming a canal (75) that provides a protective structure around spinal cord (76).

Figure 8A:
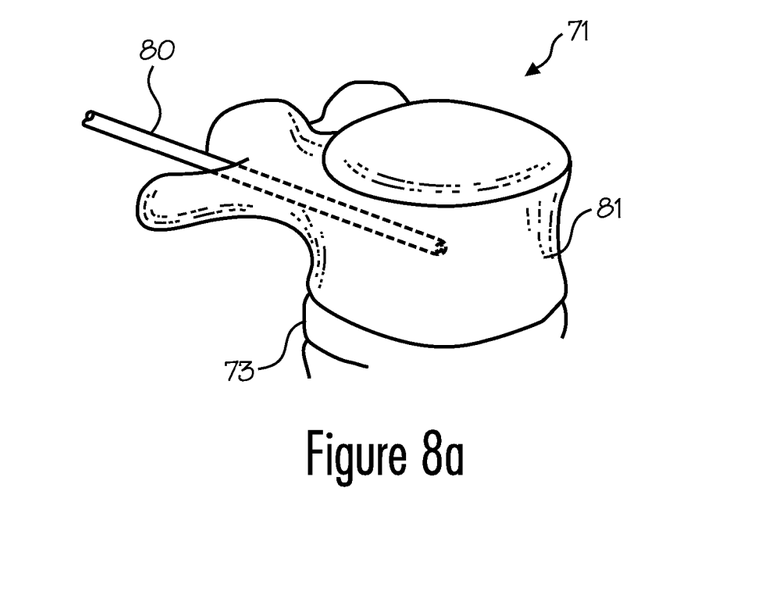
FIGS. 8(a) and (b) illustrate, respectively, perspective and axial views of portions of vertebrae undergoing an orthopedic procedure in accordance with embodiments of the present invention.
Figure 8B:
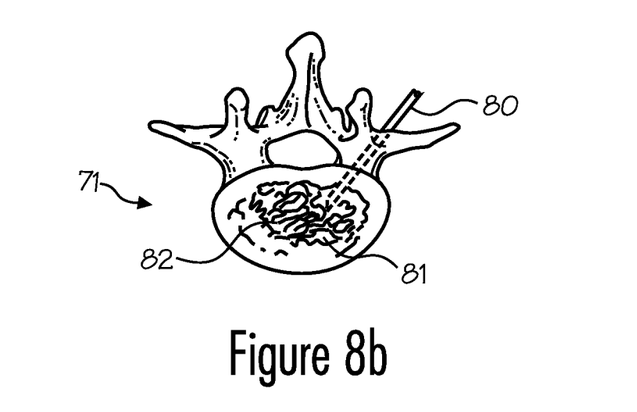

FIGS. 8(a) and (b) illustrate respective perspective and axial views of portions of a vertebra undergoing an orthopedic procedure in accordance with embodiments of the present invention. Such orthopedic procedures may be implemented to stabilize a vertebra having, for example, vertebral fractures (81). In FIG. 8(a), a needle or cannula (80) such as may be used in association with the trocar (54) mentioned above, is inserted into the damaged vertebra (71). A composition consistent with embodiments of the present invention is injected into the vertebral cavity (81) using a dispensing device coupled to the needle or cannula (80). As described above in regards to FIG. 3, such coupling mechanism may include extension tubing (40). Once injected, the composition flows to fill the cavity (81) as shown in FIG. 8(*b*). The dispensed composition then cures in situ to form a solid but flexible material (82), which stabilizes fractures or other damage to the vertebra.

While particular embodiments of the present invention have been described, those skilled in the art will recognize changes and modifications that can be made without departing from the spirit and scope of the teachings of this invention. The specification and examples are thus exemplary only, with the true scope and spirit of the invention being set forth in the following claims and legal equivalents thereof.

What is claimed is:

1. A multi-state composition for treating a damaged orthopedic structure in situ within a body having a body temperature, the composition having a first state with a first viscosity and a first shape and a second state with a second viscosity and a second shape, wherein the second shape is different than the first shape, wherein the second viscosity is greater than the first viscosity, the composition in the first state with the first viscosity comprising a separate component A and a separate component B outside the body wherein:
   component A includes one or more polysiloxanes and one or more catalysts including a platinum catalyst; and
   component B includes one or more polysiloxanes and one or more cross-linking agents;
   such that when separate component A is subsequently combined with separate component B in the damaged orthopedic structure within the body, the composition cures at the body temperature in situ within the body using the body temperature to facilitate curing thereby transforming component A and component B into a cured composition, the cured composition comprising the second state with the greater second viscosity having a Shore A durometer value in the range of 15 to 90, wherein the cured composition adheres to the damaged orthopedic structure, and wherein when the cured composition is transformed into the second shape defined by the damaged orthopedic structure, and further wherein the cured composition provides structural support to the damaged orthopedic structure,
   wherein:
   component A comprises:
      from 50% to 75% by weight of blended polysiloxanes;
      from 10% to 30% by weight of amorphous silica; and
      greater than 0.001% by weight of platinum catalyst; and
   component B comprises:
      from 50% to 75% by weight of blended polysiloxanes;
      from 10% to 30% by weight of amorphous silica; and
      from 0.5% to 5% by weight of cross-linking agent.

2. The composition of claim 1 wherein the cross-linking agent is trimethyl methyl-hydro dimethyl siloxane.

3. The composition of claim 1 wherein the blended polysiloxanes comprise a mixture of vinyldimethyl terminated dimethyl polysiloxane and trimethylsiloxy terminated polydimethyl siloxane.

4. The composition of claim 3 wherein the vinyldimethyl terminated dimethyl polysiloxane and trimethylsiloxy terminated polydimethyl siloxane are mixed in a weight ratio of approximately 1:1.

5. The composition of claim 1 wherein the catalyst comprises elemental platinum.

6. The composition of claim 1 that further comprises from 10% to 40% by weight of a radiopaque additive.

7. The composition of claim 1 that further comprises 15% by weight of a radiopaque additive.

8. The composition of claim 6 wherein the radiopaque additive is selected from one or more of the group consisting of silver powder, barium sulfate, bismuth trioxide, zirconium dioxide, tantalum powder, tantalum fiber, titanium powder, titanium fiber, calcium sulfate, calcium phosphate, hydroxyapatite, tri-calcium phosphate, gadolinium, iodine, and combinations thereof.

9. The composition of claim 1 wherein the weight ratio of component A to component B is in the range of 0.1:1 to 1:0.1.

10. The composition of claim 1 wherein the weight ratio of components A and B is approximately 1:1.

11. The composition of claim 1 having a viscosity of between 110,000 cps and 180,000 cps.

12. A composition for treating a damaged orthopedic structure in situ, the composition comprising a component A and a component B wherein:
   (a) component A includes one or more polysiloxanes and one or more catalysts including a platinum catalyst; and
   (b) component B includes one or more polysiloxanes and one or more cross-linking agents;
   the composition when cured in situ having a Shore A durometer value in the range of 15 to 90;
   the composition further comprising from 10% to 40% by weight of a radiopaque additive, wherein the radiopaque additive is selected from one or more of the group consisting of silver powder, barium sulfate, bismuth trioxide, zirconium dioxide, tantalum powder, tantalum fiber, titanium powder, titanium fiber, calcium sulfate, calcium phosphate, hydroxyapatite, tri-calcium phosphate, gadolinium, iodine, and combinations thereof.

* * * * *